US006918284B2

(12) United States Patent
Snow et al.

(10) Patent No.: US 6,918,284 B2
(45) Date of Patent: Jul. 19, 2005

(54) INTERCONNECTED NETWORKS OF SINGLE-WALLED CARBON NANOTUBES

(75) Inventors: Eric S. Snow, Springfield, VA (US); Jamie P. Novak, Alexandria, VA (US); Paul M. Campbell, Alexandria, VA (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 10/657,776

(22) Filed: Sep. 8, 2003

(65) Prior Publication Data

US 2004/0192072 A1 Sep. 30, 2004

Related U.S. Application Data

(60) Provisional application No. 60/465,218, filed on Apr. 25, 2003, and provisional application No. 60/456,536, filed on Mar. 24, 2003.

(51) Int. Cl.[7] .................. G01N 37/00; H01L 27/00; H01L 29/66
(52) U.S. Cl. .............. 73/31.05; 257/414; 257/288; 977/DIG. 1
(58) Field of Search .................. 438/48, 49, 800; 73/31.05, 31.06; 324/71.1; 977/DIG. 1; 257/213, 288, 414, 798

(56) References Cited

U.S. PATENT DOCUMENTS

| 6,346,189 | B1 | | 2/2002 | Dai et al. | |
|---|---|---|---|---|---|
| 6,528,020 | B1 | * | 3/2003 | Dai et al. | 422/98 |
| 2002/0158342 | A1 | * | 10/2002 | Tuominen et al. | 257/784 |
| 2002/0172639 | A1 | * | 11/2002 | Horiuchi et al. | 423/447.2 |
| 2002/0179434 | A1 | | 12/2002 | Dai et al. | |
| 2003/0058697 | A1 | * | 3/2003 | Tour et al. | 365/200 |
| 2003/0068432 | A1 | * | 4/2003 | Dai et al. | 427/58 |
| 2003/0098640 | A1 | * | 5/2003 | Kishi et al. | 313/309 |
| 2003/0198812 | A1 | * | 10/2003 | Rueckes et al. | 428/408 |
| 2004/0041154 | A1 | * | 3/2004 | Watanabe et al. | 257/77 |
| 2004/0067530 | A1 | * | 4/2004 | Gruner | 435/7.1 |
| 2004/0104129 | A1 | * | 6/2004 | Gu et al. | 205/775 |

FOREIGN PATENT DOCUMENTS

JP 2004-090208 3/2004

OTHER PUBLICATIONS

Wind et al., "Vertical Scaling of Carbon Nanotube FieldEffect Transistors Using Top Gate Electrodes", Amer. Inst. of Physics, May 20, 2002, vol. 80 No. 20, pp. 3817–3819.

Varghese et al, "Gas Sensing Characteristics of Multi–Wall Carbon Nanotubes", Elsevier Science B. V., 2001, pp. 32–41.

(Continued)

*Primary Examiner*—Evan Pert
(74) *Attorney, Agent, or Firm*—John J. Karasek; Joseph T. Grunkmeyer

(57) ABSTRACT

An electronic device having an interconnected network of carbon nanotubes on the surface of a substrate, and two or more electrical leads. The network forms an electrical connection between the leads.

38 Claims, 7 Drawing Sheets

OTHER PUBLICATIONS

Kinney, "NRL Scientists Discover New Approach to se Carbon Nanotubes in Electronics and Bio–Chemical Sensors", Labstracts, Apr. 21, 2003.

Shim et al., "Polymer Functionalization for Air–Stable n–Type Carbon Nanotube Field–Effect Transistors", Amer. Chem. Society, 2001, vol. 123, pp. 11512–11513.

Fuhrer et al, "Crossed Nanotube Junctions", Science Magazine, Apr. 21, 2000, vol. 288, pp. 494–497.

Shiraishi et al, "Conduction Mechanism in Single–Walled Carbon Nanotubes", Elsevier Science B.V., 2002, vol. 128, pp. 235–239.

Grigorian et al, "Transport Properties of Alkali–MetalDoped Single–Wall Carbon Nanotubes", The Amer. Physical Society, Aug. 15, 1998, 3rd series, vol. 58, No. 8, pp. 4195–4198.

Kong et al, "Nanotube Molecular Wires as Chemical Sensors", Science Magazine, Jan. 28, 2000, vol. 287, pp. 622–625.

Dai et al., "Carbon Nanotube Sensor Device" U.S. Provisional Appl. No. 60/171,200, filed Dec. 15, 1999.

Gu et al., "Nanotube Gas Sensor Based on Work Function Electrodes" U.S. Provisional Appl. No. 60/429,712, filed Nov. 27, 2002.

* cited by examiner-

INTERCONNECTED NETWORKS OF SINGLE-WALLED CARBON NANOTUBES is application claims the benefit of U.S. Provisional Patent Application No. 60/456,536 filed on Mar. 24, 2003 and U.S. Provisional Patent Application No. 60/465,218 filed on Apr. 25, 2003, both incorporated by reference.

BACKGROUND OF THE INVENTION

1. Field of the Invention

The invention relates generally to materials useful as components of electronic devices such as transistors.

2. Description of the Prior Art

Because of their unique structural, mechanical and electrical properties, materials containing single-wall carbon nanotubes (SWCNTs) have been developed for electronic and sensor applications. However, two major obstacles have stood in the way of commercial electronic applications. The first obstacle is lack of position and orientation control. Such control is necessary for high-yield device fabrication. The second problem is lack of control of the precise atomic structure of SWCNTs. SWCNTs are currently produced with a range of diameters and different chiralities. These variations in atomic structure result in a wide variety of electronic properties ranging from semiconducting to metallic behavior. There has been little progress in solving either of these two problems that currently prohibit high yield device fabrication.

One electronic property of SWCNTs is the high room temperature mobility of semiconducting SWCNTs (s-SWCNTs) that is more than an order of magnitude larger than the mobility of crystalline Si. This high mobility has prompted fabrication and study of field-effect transistors in which a single s-SWCNT serves as a high-mobility transport channel. Such devices can have a transconductance per unit channel width greater than that of state-of-the-art Si transistors. However, because of the limited current-carrying capacity of individual SWCNTs, many s-SWCNTs aligned side by side in a single device would be required in order to surpass the current drive of a Si device. Such precise positioning of SWCNTs is beyond the capability of current growth and assembly technology and presents a major technological hurdle for carbon nanotube-based electronic applications.

SUMMARY OF THE INVENTION

The invention comprises an electronic device comprising an interconnected network of carbon nanotubes (CNTs) on the surface of a substrate, and two or more electrical leads. The network forms an electrical connection between the leads. The invention further comprises a device comprising an interconnected network of nanofilaments on the surface of a substrate, and two or more electrical leads.

DETAILED DESCRIPTION OF THE EXAMPLE EMBODIMENTS

Interconnected Network of Carbon Nanotubes

Figure 1:
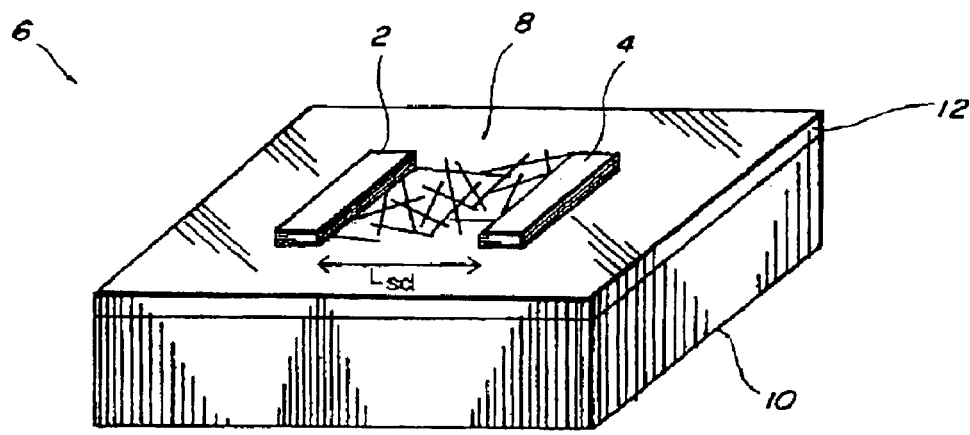
FIG. 1 schematically illustrates a transistor incorporating an interconnected network of SWCNTs.

In one embodiment, a substrate, two or more electrical leads, and a very dilute interconnected network or array of CNTs are used. The nanotubes form a network in that they contact each other, such that continuous electrical pathways are formed between the leads. This differs from the situation where one or more individual nanotubes contact both leads. This also differs from the situation where the CNTs form a dense mat with little open space. The network may contain SWCNTs, multi-wall carbon nanotubes (MWCNTs), or both. SWCNTs typically contain a mixture of semiconducting SWCNTs (s-SWCNTs) and metallic SWCNTs (m-SWCNTs), which may be suitable for applications that depend on a changing conductivity of the network. The conductivity of MWCNTs can vary with the wall thickness, the number of walls in the tubes. Tubes with 2–3 walls may have semiconducting behavior, while more walls can make the tubes metallic. The electrical properties of the network can depend on the proportion of s-SWCNTs, m-SWCNTs, and MWCNTs of different wall thicknesses in the network.

The network may be dilute enough such that at least 75% or substantially all the CNTs are at least partially in contact with the substrate. The adhesion of the tubes to the substrate can be better than the adhesion of the tubes to each other. This can allow the network and substrate to be processable without the network being removed from the substrate. This differs from "carbon nanotube paper" which has little cohesive strength and can easily be removed from a substrate by processing, as most of the tubes are not adhered to it. This adhesion of the network can also help to press an upper, crossing CNT onto the CNT below it, which can improve the conductivity of the junction between the CNTs. Suitable densities include, but are not limited to, at most about 100 $\mu m^{-2}$, at most about 50 $\mu m^{-2}$, at most about 10 $\mu m^{-2}$, and at least about 0.3 $\mu m^{-2}$. Suitable thicknesses for the network include, but are not limited to, up to about 100 nm and up to about 10 nm. The network can be a sub-monolayer of carbon nanotubes, meaning that there is open space between the nanotubes leaving portions of the substrate exposed. The network may be substantially free of other materials, or other materials may be present. Any substrate may be used, depending on the application.

Interconnected networks of CNTs can be produced either by direct growth on a catalyzed substrate or by deposition onto an arbitrary substrate from a solution of suspended CNTs. No attempt is made to orient the nanotubes with respect to each other or to the leads. Such networks are easily patterned into devices of arbitrary size and geometry with high yield. The leads may be on the surface of the substrate with the network. The leads may be formed by any means known in the art including, but not limited to, photolithographic techniques.

If the density of CNTs in the network is sufficiently high, the nanotubes will interconnect and form continuous electrical paths. The density of CNTs may be near the percolation threshold for electrical conduction. It is in this dilute limit that the networks exhibit semiconducting behavior, opening up a wide range of electronic and sensor applications. At low nanotube densities (~1 $\mu m^{-2}$) the networks may be electrically continuous and behave like a p-type semiconductor with a field-effect mobility of ~10 $cm^2/V$ s and a transistor on-to-off ratio ~$10^5$. This field-effect mobility is approximately an order of magnitude larger than the mobility of materials typically used in commercial thin-film transistors, e.g., amorphous Si. At higher densities ~10 $\mu m^{-2}$ the field-effect mobility can exceed 100 $cm^2/V$ s; however, in this case the network behaves like a narrow band gap semiconductor with a high off-state current.

These mobility values and correspondingly good electronic quality of the CNT network may be due to a combination of the low resistance of inter-CNT contacts and the high mobility of the individual CNTs, which together compensate for the extremely low fill factor of the network.

Fuhrer et al., "Crossed Nanotubes Junctions," *Science* 288, 494 (2000), incorporated by reference, have shown that the intersection of two s-SWCNTs or two metallic SWCNTs forms a good electrical contact with an electrical conductance ~0.1 $e^2/h$ and that the intersection of a metallic and a s-SWCNT forms a Schottky barrier with a barrier height approximately equal to ½ band gap of the s-SWCNT. Consequently, highly interconnected SWCNT arrays can be electrically continuous with electronic properties that depend on the level of interconnectivity and on the electronic properties of the constituent SWCNTs.

This system of electrically connected randomly positioned CNTs is in many ways analogous to the two-dimensional random resistor networks studied in percolation theory. Such resistor networks are electrically conducting if the density of connected resistors exceeds a percolation threshold. In addition, the sample-to-sample variations are vanishingly small if the size of the resistor lattice is large compared to the lattice spacing. In the present case it is estimated that the percolation threshold will correspond approximately to the density at which the average distance between nanotubes, $1/\rho^{1/2}$, equals their average length, i.e., $\rho_{th} \sim 1/<L>^2$ the network properties will be relatively uniform provided that the device dimensions are much larger than $1/\rho^{1/2}$. Above the percolation threshold, there is a high likelihood that the CNTs will intersect with one another and form continuous electrical paths.

The network may also comprise a filler material such as a polymer. The network may alter the electrical properties of the filler. Alternatively, the filler may be only a support that is not used for its electrical properties.

Transistor

In another embodiment, the network and leads form a field-effect transistor. This may require three leads, which are the source, drain, and gate. The network is the conduction channel between the source and the drain. The gate may be the substrate or it may be deposited on an insulating layer on the network. Useful device properties can be achieved without precision assembly of the nanotubes. Interconnected networks of CNTs can exhibit semiconducting behavior with a field-effect mobility of >10 $cm^2/Vs$ and an on-to-off ratio >$10^5$.

CNT networks can be deposited or grown onto a wide range of noncrystalline and compliant substrates. The high mobility of CNT networks is superior to the mobility found in commercially available thin-film transistor materials, and the ability to deposit CNT networks onto arbitrary substrates opens new possibilities for electronic applications. For example, amorphous Si, commonly used as the active electronic material in flat-panel displays, has a mobility of 1 $cm^2/Vs$ and can only be deposited at high temperatures prohibiting the use of plastic substrates. Consequently, solution deposition of interconnected networks of CNTs onto plastic substrates would offer the potential of lighter, less breakable, and higher performance flat panel displays. In addition, CNT networks are flexible and can conform to arbitrary geometries. This capability opens the possibility of placing active electronics on flexible sheets or in fabrics. CNT networks are also optically transparent which may also be of use in display technology.

Because the networks consist of both semiconducting and metallic nanotubes, if the density of metallic nanotubes exceeds the percolation threshold then the network will become metallic. The electronic properties of the network can range continuously from semiconducting to metallic as a function of density. The value of the density that corresponds to particular electronic property is a function of the average length of the nanotubes and the fraction of nanotubes that are metallic. The electronic properties can be composition- and density-tunable. A suitable density range includes, but is not limited to, a maximum of about $0.1/<L>^2$ or $1/<L>^2$ to a minimum of about $100/<L>^2$ or $1000/<L>^2$. In order to achieve the highest current drive with good off-state characteristics, the fraction of both metallic and large diameter nanotubes may have to be reduced. Current growth technology of SWCNTs yields approximately 30% metallic SWCNTs. A suitable range of m-SWCNT density includes, but is not limited to, up to $1/<L>^2$, independent of the density of s-SWCNTs. The reduction of this fraction of m-SWCNTs requires control over the chirality of the SWCNTs during growth or some post-growth means of separating metallic from semiconducting nanotubes. Alternatively, Collins et al., "Engineering Carbon Nanotubes and Nanotube Circuits Using Electrical Breakdown," *Science* 292, 706 (2001), incorporated by reference, have shown that applying a large source-drain bias while gating off any semiconducting nanotubes can selectively burn metallic (and possibly low band gap semiconducting) nanotubes. This technique may work as well with nanotube networks to remove those conduction paths that limit the device turn-off characteristics.

The nanotube networks may be formed by direct growth of the nanotubes on the substrate, or by depositing previously grown CNTs onto the substrate. The deposition method allows the fabrication of thin-film transistors without exposing the substrates to high temperatures, thus permitting a wide variety of substrates, including plastic and compliant substrates. Because several techniques have been demonstrated for selectively converting s-SWCNTs from p- to n-type for complementary logic applications, it is likely that interconnected networks can be selectively converted to n-type for such applications as well.

Sensor

In another embodiment, CNTs are used for sensor applications by serving as a sensitive electronic transducer of chemical recognition events. SWCNTs are composed entirely of surface atoms while exhibiting transport properties superior to single crystalline Si. The high surface-to-volume ratio of SWCNTs translates into increased sensitivity and the chemical inertness of SWCNTs makes them very robust for operating in corrosive environments. These features make them suitable for molecular sensors, including both chemical and biological sensors. It has been demonstrated that individual semiconducting SWCNT devices produce a large resistance change in response to certain types of gaseous analytes. In such sensors, the adsorption of an analyte molecule with strong electron donor or acceptor properties results in a charge transfer between the analyte and the nanotube that changes its electrical resistance. Such sensors, using SWCNTs that connect to both leads, have detected 0.1 part per billion (ppb) of $NO_2$ which is superior to current state-of-the-art $NO_2$ sensors by several orders of magnitude. (Qi et al., "Toward Large Arrays of Multiplex Functionalized Carbon Nanotubes Sensors for Highly Sensitive and Selective Molecular Detection," *Nano Lett.* 3, 347 (2003), incorporated by reference.) The ability to obtain semiconducting networks is important because metallic networks are less sensitive to the charge perturbations caused by molecular adsorption.

Because chemical nerve agents also have strong electron transfer properties, carbon nanotube-based devices are suitable for extremely high performance chemical agent detectors. A device or transistor as described above can be used, where the network can be exposed to a gaseous sample. The device may be used to detect dimethyl methylphosphonate (DMMP), a simulant that is chemically similar to the nerve agent sarin. DMMP readily adsorbs on CNTs resulting in a transfer of negative charge to the nanotube that manifests itself as an increase in resistance or as a shift of the transistor threshold voltage. The molecular adsorption is reversible by applying a small positive gate bias that releases the DMMP from the nanotube surface.

The shift in threshold voltage caused by DMMP indicates a new electronic transduction method for the detection of sarin and potentially other gaseous nerve agents that have strong electron donating properties. Previous reports of nanotube sensors have used the change in device current as the electrical transduction mechanism. However, detecting the threshold voltage shift directly has advantages in many applications. The threshold voltage shift is directly proportional to the amount of charge transfer, which in turn is proportional to the number of adsorbed molecules. Consequently, the voltage shift will have a linear dependence on dose up until saturation of the adsorption sites causes nonlinearities. In addition, the magnitude of the threshold shift is relatively insensitive to the details of the nanotubes in the device, whereas a change in current can vary greatly depending on the number and type of nanotubes.

The CNTs in the sensor may be treated with a polymer that selectively absorbs the analyte to be detected. Alternatively, the sensor may be operated in conjunction with a filter treated with such a polymer to remove the analyte. The filter may be used to establish a reference measurement in the absence of the analyte.

A Si MOSFET cannot be operated in an aqueous saline solution, however CNT networks can be operated in such an environment. This capability opens the possibility of using biologically functionalized networks for the label-free transduction of biological recognition events. This approach can be used to electronically detect the adsorption of a protein from solution onto a SWCNT network.

Nanofilaments

In another embodiment, other kinds of nanofilaments are used instead of carbon nanotubes. Most metals and semiconducting materials can be made into nanofilaments. A network of such nanofilaments may have electrical properties similar to a network of carbon nanotubes. Networks of such nanofilament materials may be better suited for some specific applications.

Having described the invention, the following examples are given to illustrate specific applications of the invention. These specific examples are not intended to limit the scope of the invention described in this application.

EXAMPLE 1

Formation of interconnected networks—An iron-based catalyst for the nanotube growth was deposited on a Si wafer with a 250-nm-thick thermal oxide by dipping the substrates in a ferric nitrate nonahydrate isopropanol solution for 10 s followed by a 10 s rinse with hexane. The density of nanotubes was controlled by varying the concentration of the catalyst solution from 1.5 to 150 mg/L. Immediately after catalyst deposition, the samples were placed into a furnace and purged with a mixture of argon and hydrogen. The samples were then heated to 800° C. and annealed for 30 min. SWCNT growth was initiated by the introduction of ethylene (5 $cm^3$/min) into the Ar (600 $cm^3$/min)-$H_2$ (400 $cm^3$/min) carrier gas flow for 10 min. The samples were then cooled in flowing Ar gas.

EXAMPLE 2

Fabrication of transistors—A schematic of the device is shown in FIG. 1. Source 2 and drain 4 electrodes were fabricated on the substrate 6 having the network 8 from Example 1 using optical lithography and lift-off of a 150-nm-thick Ti film. The regions of the devices between the source-drain electrodes were then covered with photoresist and the nanotubes outside this protected area were removed by using a $CO_2$ snow jet. Finally, the protective photoresist was removed. The Si wafer 10, having a $SiO_2$ layer 12, was used as the gate. The device geometry was varied with the source-drain channel length, $L_{sd}$, ranging from 1 to 25 $\mu$m and the channel width, W, ranging from 35 to 100 $\mu$m. An atomic force microscope (AFM) image of a CNT network in the region between the source-drain electrodes was made. Such images and AFM line profiles were used to determine the diameter (d), density ($\rho$), and length (L) of the nanotubes where $\rho$ is defined as the number of CNTs per unit area. For these growth conditions, <L> ranged from 1 to 3 $\mu$m.

EXAMPLE 3

Electrical properties of transistors—The transistors from Example 2 were tested in a vacuum probe station. Networks were electrically conducting for CNT densities exceeding ~0.3 $\mu m^{-2}$. For most of the devices, the average nanotube length, <L>, was much shorter than $L_{sd}$, which means that the source-drain current flowed through a series of inter-nanotube contacts.

Figure 2:
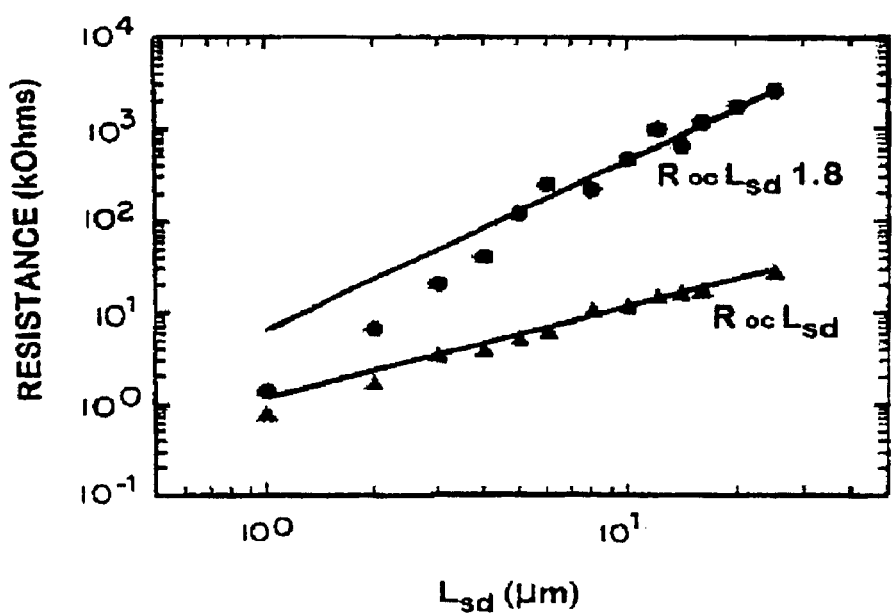
FIG. 2 is a graph of source-drain resistance vs. source-drain distance at two different densities of SWCNTs.

The geometric scaling of the device resistance is shown in FIG. 2 which plots the log of the source to drain resistance versus log($L_{sd}$) for two sets of devices corresponding to $\rho$=10 and 1 $\mu m^{-2}$. The resistance data for the 10 $\mu m^{-2}$ network scaled linearly with channel length with a sheet resistance of 108 k$\Omega$/square. The resistance data for the 1 $\mu m^{-2}$ network scaled nonlinearly with channel length, and a least squares power law fit to the data for $L_{sd} \geq 5$ $\mu$m yielded $R \propto L^{1.8}$. This nonlinear scaling is an indication that the network is approaching the percolation threshold where nonlinear effects are expected. Note that the short channel length devices with $L_{sd} \sim \langle L \rangle$ scaled more rapidly with $L_{sd}$. In these devices, individual CNTs can directly bridge the source-drain electrodes and thus lower the resistance.

Figure 3:
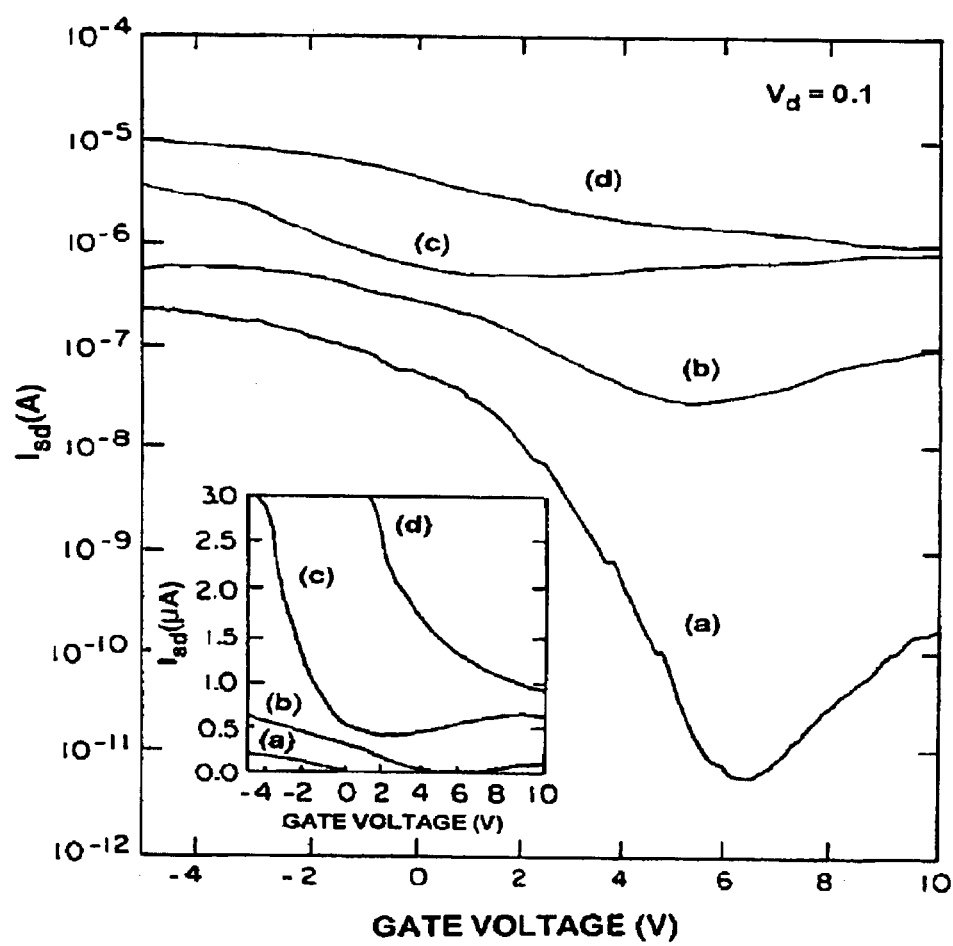
FIG. 3 is a graph of source-drain current vs. source-drain voltage for four different devices having SWCNTs.

The above resistance data establish that the intersecting CNTs form an electrically continuous interconnected network. The gate response of $I_{sd}$ was measured to determine whether the networks exhibited a semiconducting or metallic behavior. FIG. 3 [curve (a)] plots the transistor characteristics for the $\rho=1$ $\mu m^{-2}$ network with device dimensions of $L_{sd}=10$ $\mu m$ and $W=35$ $\mu m$. This device exhibited an on-to-off ratio of ~$10^5$ and a threshold voltage of 2 V. The observed field effect is likely a combination of two effects: the field dependence of the carrier concentration in the s-SWCNTs and the gating of the Schottky barriers present at the nanotube/Ti contacts and at the semiconductor/metallic inter-nanotube contacts. The magnitude and polarity of the gate dependence indicate that the network behaves like a p-type semiconducting thin film. The standard formula, $\mu_{eff}=dI_{sd}/dV_g/L_{ox}L_{sd}/\epsilon V_{sd}W$, defines an effective mobility for the network where $L_{ox}$ and $\epsilon$ are the thickness and dielectric constant of the $SiO_2$ gate oxide. For this network, $\mu_{eff}=7$ $cm^2/Vs$, which is a typical value for devices with high on-off ratio, although occasionally values as high as 50 $cm^2/V\,s$ were measured. For comparison, these values are about an order of magnitude larger than the mobility of amorphous Si ($\mu_{eff} \approx 1$ $cm^2/Vs$), a material commonly used in commercial thin film transistor applications. Note that $I_{sd}$ reaches a minimum at $V_g \approx 6$ V and then increases for larger gate bias. This reversal in slope indicates that the gate potential has inverted some of the electrical paths to n-type conduction. Such inversion from p-type to n-type conduction has been previously noted in field-effect measurements on individual s-SWCNTs and establishes a lower limit to the off-state current.

Also plotted in FIG. 3 are data from three other devices [curves (b), (c), and (d)] fabricated using networks with $\rho>3$ $\mu m$. The linear gate dependence of the on-state current (see inset) yields field-effect mobilities ranging from 17 to 270 $cm^2/V\,s$. However, in each of the devices the on-to-off ratio is $\leq 10$. In these devices, the increase in on-state current is achieved at the expense of a high off-state current which in curves (b) and (c) are caused by inversion to n-type conduction. This high off-state current occurred in all of the tested devices with either high densities, $\rho \geq \rho_{th}$, or short channel lengths, $L_{sd} \sim \langle L \rangle$. The inversion to n-type conduction at low gate bias accompanied by a high off-state current is consistent with the behavior of a narrow band gap semiconductor. The high off-state current in these devices is attributed to continuous paths of narrow band gap and metallic nanotubes.

The band gap of a s-SWCNT scales inversely with its diameter. It is therefore postulated that the high off-state current of dense networks is caused by continuous paths of large diameter (>2 nm) and metallic nanotubes. In such cases, the density of metallic and large-diameter SWCNTs exceeds the percolation threshold and forms continuous paths across the device. Consequently, the off-state current in networks will be dominated either by the largest diameter s-SWCNTs or by metallic nanotubes, provided their density exceeds $\rho_{th}$. From AFM line traces, $\langle d \rangle=1.7$ nm and that approximately one third of the nanotubes in the network had a diameter >2 nm corresponding to a band gap <0.35 eV. At high nanotube densities, the density of narrow band gap nanotubes can exceed $\rho_{th}$ and the network will form narrow-band gap conduction paths.

These data suggest that it should be possible to improve the off-state current by reducing the fraction of large-diameter nanotubes. Li et al. have shown that the diameter of a single-wall nanotube is approximately equal to the diameter of its catalyst particle. Consequently, one key to higher density nanotube networks with improved on-to-off ratio is careful control of the catalyst particle size.

EXAMPLE 4

Testing as sensor—Transistors as made in Example 2, were exposed to DMMP. Concentrations of DMMP were created using a calibrated permeation tube with nitrogen used as the carrier gas. Dilutions of DMMP were performed using electronic mass flow controllers.

Figure 4:
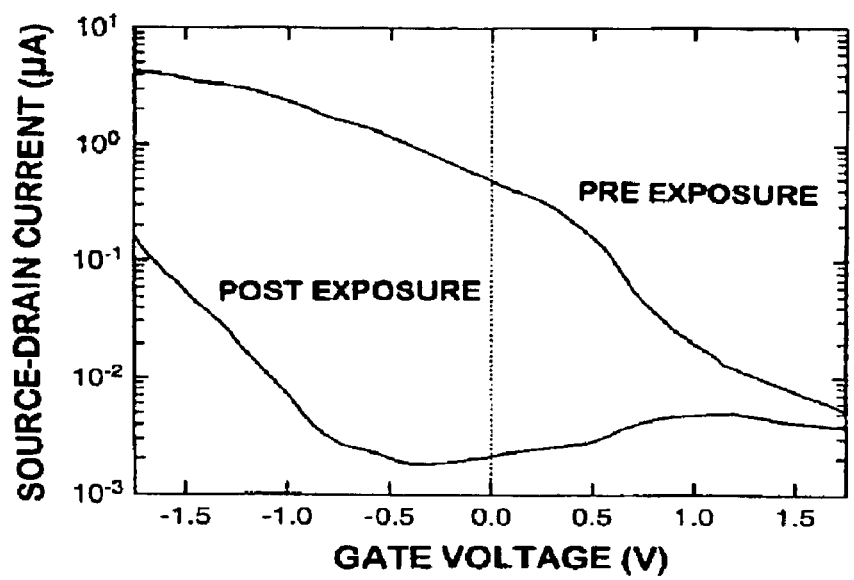
FIG. 4 is a graph of the source-drain current versus gate voltage for a chemiresistive flow cell before and after exposure to a dose of DMMP.

FIG. 4 shows a plot of the source-drain current versus gate voltage for a thin-film transistor before and after exposure to a dose of DMMP. The onset of current in the post-exposure data was shifted by about ~2 V relative to the pre-exposure curve. Such a shift of the threshold voltage has been observed in other CNT devices and is caused by a charge transfer between the adsorbed molecules and the nanotube. The shift to negative voltage indicates that the adsorption of DMMP produces a negative charge on the nanotubes, i.e. additional positive charge from the gate bias is required to offset the negative charge transferred from the DMMP. The electron transfer is consistent with the fact that DMMP is a strong electron donor through the partial negative charge on its carbonyl.

In order to use the threshold shift as the electronic transduction mechanism, a feedback circuit that adjusted the gate voltage on the transistor was provided in order to maintain a constant source-drain current. In this mode of operation, the detected change in gate voltage was proportional to the number of adsorbed molecules of DMMP.

Figure 5:
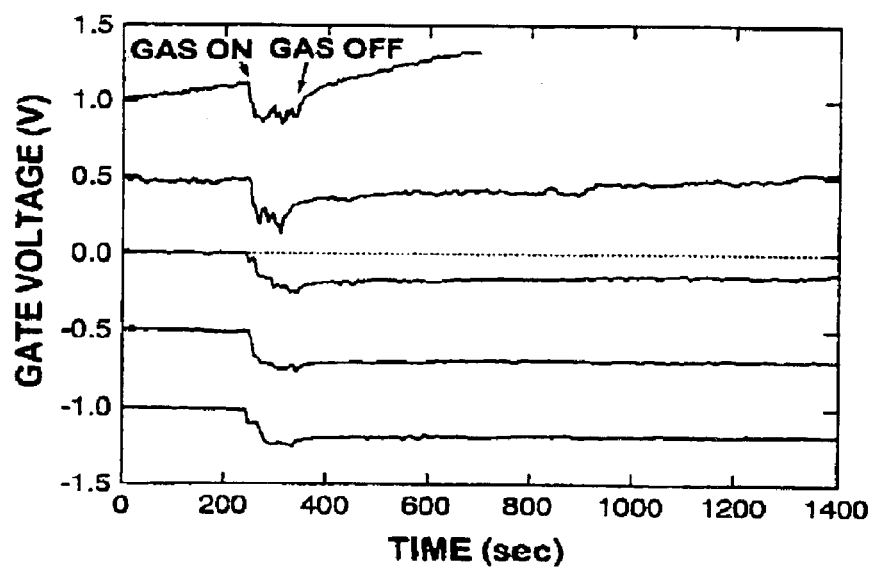
FIG. 5 is a graph of the time dependence of the gate voltage of a sensor in response to small doses of DMMP.

FIG. 5 shows the time dependence of the gate voltage of one such detector in response to small doses of DMMP. The five traces correspond to operation of the sensor at an initial gate bias of 1, 0.5, 0, −0.5 and −1 V. In each case when the device is exposed to the DMMP the feedback circuit produces an additional negative gate bias in order to compensate for the shift in threshold voltage caused by the DMMP. Note that over the time scale of the experiment the −1, −0.5 and 0 V curves did not recover to the initial value of the gate bias, which indicates that the desorption time of the DMMP was greater than 1000 s. However, when the sensor was biased at positive voltage, the desorption rate of the DMMP was increased and the initial device characteristics can be fully recovered. Such recovery has been difficult to achieve in other examples of nanotube sensors and either high temperatures or ultraviolet light has been necessary to desorb the analyte molecule. It may be that in the case of positive bias, the gate potential decreases the desorption activation energy, which in turn controls the recovery time of the sensor.

Note that at +1 V gate bias, not only does the device recover quickly; the background voltage steadily drifts to higher voltage. This background drift is caused by a positive feedback of gate-bias-induced charging of the gate oxide. Application of a positive gate bias causes a charging of the gate oxide due to the high fields in the vicinity of the nanotube. This charging screens the gate field causing an increase in the source-drain current. The feedback circuit reacts to this increase by further increasing the gate bias causing additional charging. For this reason the devices are best operated at small negative gate bias. Under such bias conditions, the sensor integrates the dose of DMMP up until which time the sensor is refreshed by applying a pulse of positive gate bias to desorb any collected DMMP.

Figure 6:
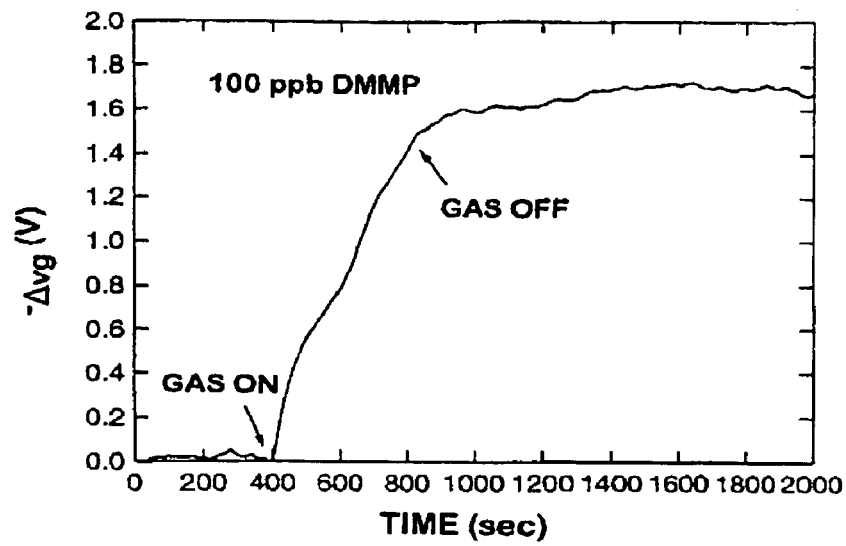
FIG. 6 is a graph showing the temporal response of a SWCNT transistor sensor to an exposure of DMMP.

In order to calibrate the response of the detectors the probe chamber was flushed with 100 ppb by volume of DMMP at a flow rate of 1 L/min. FIG. 6 shows the measured temporal response of the detector to such an exposure. The 400 s dose produced a gate shift of −1.9 V and the initial rate of the threshold voltage shift was ~10 mV/s. However, this initial rate is likely to be artificially low due to the fact that the gas was released into the far end of a probe chamber with a volume of 0.5 L. Consequently, the chamber would require several minutes to achieve equilibrium.

EXAMPLE 5

Figure 7:
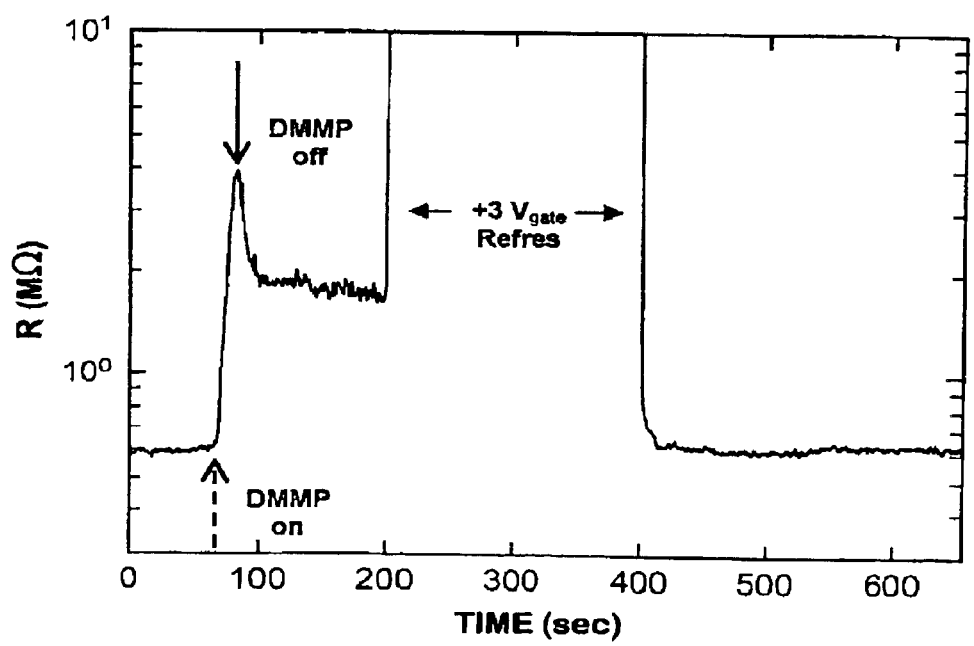
FIG. 7 displays the time dependence of the resistance of a SWCNT transistor (0 V gate bias) in response to a 10 s exposure of a concentrated dose of DMMP.

Sensor with zero gate bias—FIG. 7 displays the time dependence of the resistance of a CNT transistor (0 V gate bias) in response to a 10 s exposure of a concentrated dose of DMMP. The resistance rose rapidly as the DMMP adsorbed onto the surface of the nanotubes. After the removal of the DMMP vapor the resistance of the device initially decreased but did not fully recover. The initial rapid recovery is only observed at high dose levels and is likely caused by secondary interactions between DMMP molecules that lower the desorption energy. Following this initial partial recovery the remaining DMMP desorbs very slowly and can remain on the nanotubes for many hours. Previous nanotube sensors have required exposure to ultraviolet light or heat to desorb the analyte molecules from the surface (Kong et al., "Nanotube Molecular Wires as Chemical Sensors," *Science* 287, 622 (2000), incorporated by reference, and Qi et al.).

Rapid recovery of the sensor was achieved by applying a positive bias to the Si gate. In FIG. 7, a 3 V gate bias was applied between t=200 s and 400 s. After the gate bias was removed, the resistance returned to its pre-exposure value indicating the removal of the DMMP. This exposure and refresh process can be repeated many times without degrading the performance of the device. We postulate that the Coulomb interaction between the DMMP and the negative charge induced by the gate bias lowers the desorption barrier sufficiently to refresh the sensor at room temperature.

EXAMPLE 6

Figure 8:
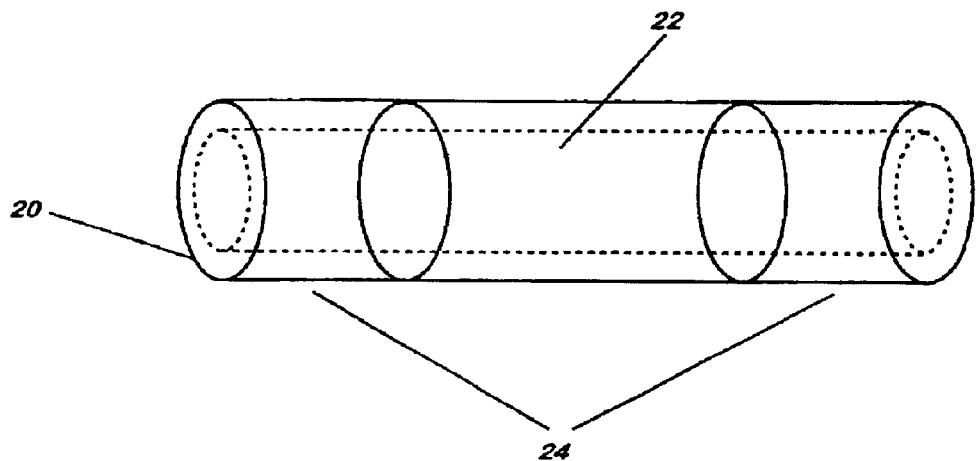
FIG. 8 schematically illustrates a chemiresistive flow cell incorporating an interconnected network.

Flow-cell sensor—Chemiresistive flow cells were fabricated from ⅛" inner diameter by 2" long quartz tubing 20. FIG. 8 schematically illustrates the device. The inner surface of the tubing was coated with CNTs 22 by sealing one end with laboratory film and filling with liquid catalyst (ferric nitrate nonahydrate, 1.5 mg/L in 2-propanol). The catalyst was then removed, rinsed with hexanes, and dried under a $N_2$ stream. Nanotubes were then grown in a tube furnace at 800° C. with Ar and H carrier gases and ethylene as the carbon source. The ends of the quartz tube were then coated with silver paint 24 to provide electrical contacts. End-to-end resistance of the flow cell was typically around 1 MΩ.

Figure 9:
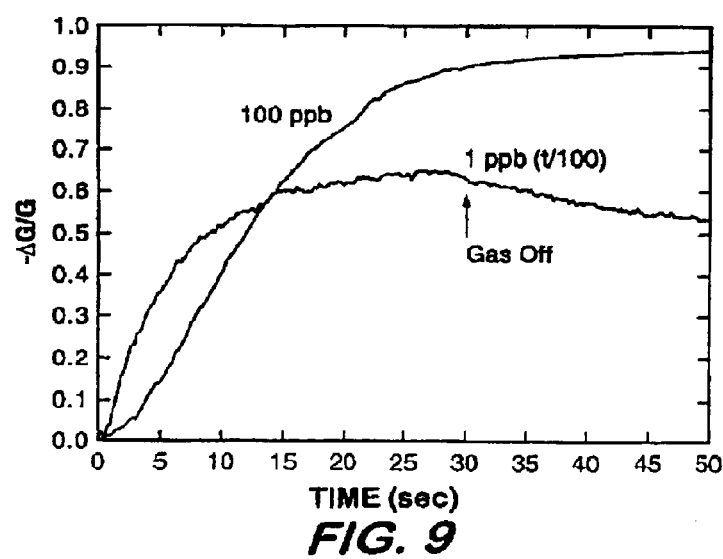
FIG. 9 is a graph of relative conductance of a flow cell chemiresistor vs. time as it is exposed to DMMP.

The chemiresistors were exposed to calibrated doses of DMMP. FIG. 9 plots the relative conductance, −ΔG/G vs. time for exposures of 1 and 100 ppb DMMP. The 100 ppb and 1 ppb concentrations were delivered for 30 s and 3000 s, respectively. (Note in the figure that the time scale of the 1 ppb exposure has been divided by a factor of 100.) The rate of change of the conductance scales linearly with the concentration of DMMP. The 100 ppb data indicate an initial delay in the response of the detector. This delay is caused by the time that is required for the concentration of DMMP to reach equilibrium in the quartz tubing. The relative conductance changes by a factor of 0.9 for the 30 s, 100 ppb dose and 0.6 for the 3000 s, 1 ppb dose. The reduced response to the 1 ppb dose indicates an approach to equilibrium where the rate of adsorption approaches the rate of desorption. Sub-ppb concentrations are easily detectable using CNT network chemiresistors. The chemiresistors completely recovered by heating them to 90° C. for 10 minutes in air.

Figure 10:
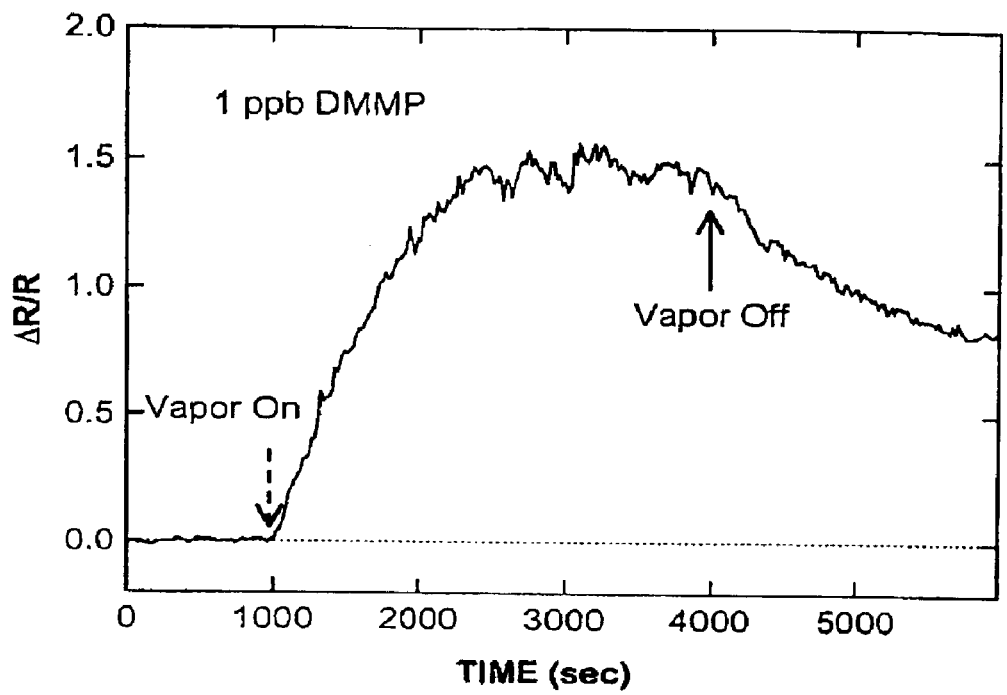
FIG. 10 plots the time dependence of the relative change in resistance, $\Delta R/R$, in a chemiresistor flow cell.

FIG. 10 plots the time dependence of the relative change in resistance, ΔR/R, in a chemiresistor flow cell for an exposure to 1 ppb DMMP that was delivered for 3000 s. The 1 ppb exposure resulted in a ΔR/R=1.5. This large value of ΔR/R relative to the background noise ($R_{noise}$/R~0.01) indicates that sub-ppb concentrations are easily detectable.

Defining the sensitivity of the response as S=(ΔR/R)/(P/$P_o$) where $P_o$ is the equilibrium vapor pressure at 20° C. ($P_o$=2.6 parts per thousand for DMMP), S=3.9×10$^6$. For comparison, the measured sensitivity to DMMP of carbon black/polymer composite chemiresistors is S=0.6 (Hopkins et al., "Detection and Classification Characteristics of Arrays of Carbon Black/Organic Polymer Composite Chemiresistive Vapor Detectors for the Nerve Agent Simulants Dimethylmethylphosphonate and Diisopropylmethylphosponate," Anal. Chem. 73, 884 (2001) incorporated by reference), a difference of more than six orders of magnitude. Another metric of performance is $EC_{50}$, the airborne concentration of a chemical agent that is sufficient to induce effects of interest in 50% of those exposed for 30 minutes. For a resting exposure to sarin, $EC_{50}$ =450 ppb (McKone et al, *Strategies to Protect the Health of Deployed U.S. Forces: Detecting, Characterizing, and Documenting Exposures* (National Academy Press, Washington, D.C., 2000, incorporated by reference).

EXAMPLE 7

Figure 11:
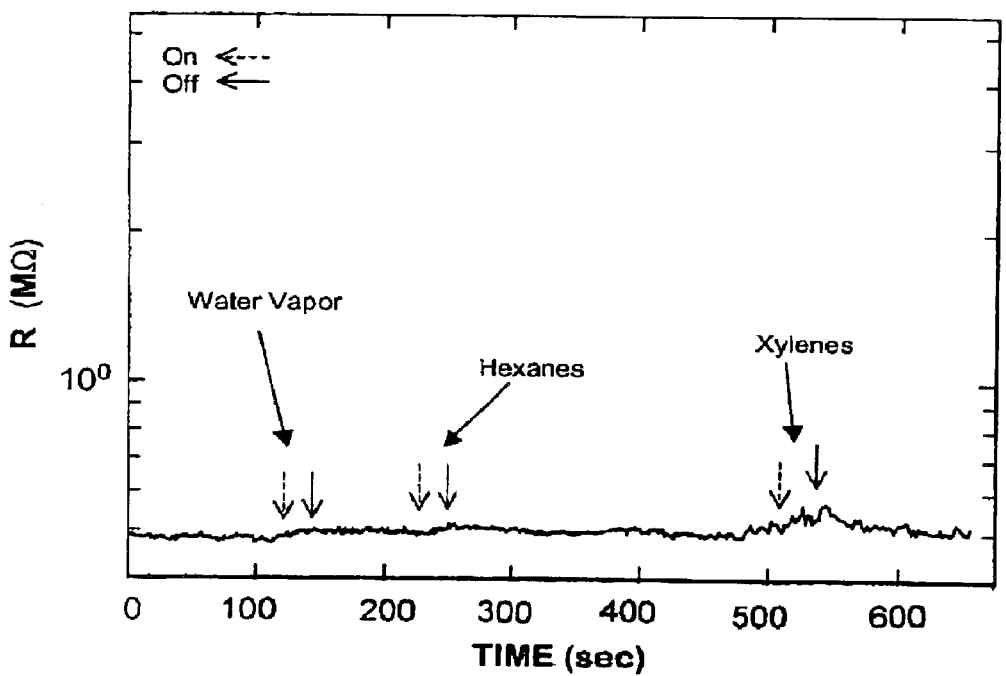
FIG. 11 shows the response of a sensor to one-minute exposures of saturated vapors of water, xylene and hexane.

Testing of interferents—Two of the most common interferents are water and fuel vapors. FIG. 11 shows the response of a sensor from Example 6 to one-minute exposures of saturated vapors of water, xylene, and hexane. Hexanes (aliphatic hydrocarbon) and xylenes (aromatic hydrocarbon) were used as simulants for gasoline and diesel fuel, respectively. These saturated vapors produced little or no resistance change indicating that CNTs are intrinsically insensitive to some of the most common interferents present in field applications.

EXAMPLE 8

Sensor with filter—In order to obtain further chemical specificity chemoselective polymers were used to filter vapors from the air flowing to the sensors from Example 6. Chemoselective polymers have been designed to concentrate the vapors of many organic analytes and can thus be used to provide additional chemical specificity to the CNT-based sensors. Such polymers have been applied to CNTs to distinguish between the adsorption of an electron-donating ($NH_3$) and an electron-withdrawing ($NO_2$) molecule (Qi et al.).

One chemoselective polymer distinguished between two electron donors, $NH_3$ and DMMP. A filter composed of glass wool coated with an acidic, strong hydrogen bonding polycarbosilane (HC) was used. The HC-coated glass wool, as well as an uncoated filter, were placed in-line with the flow of air to the sensors. In this case, the chemical selectivity is derived from two mechanisms. One mechanism is the degree of hydrogen bonding between the polymer and the two analytes. In addition, the sorption coefficient of permanent gases into a polymer film is typically much smaller than the coefficient for organic vapors. The relative response of the coated and uncoated filters was used to distinguish between the two electron donating molecules.

Figure 12:
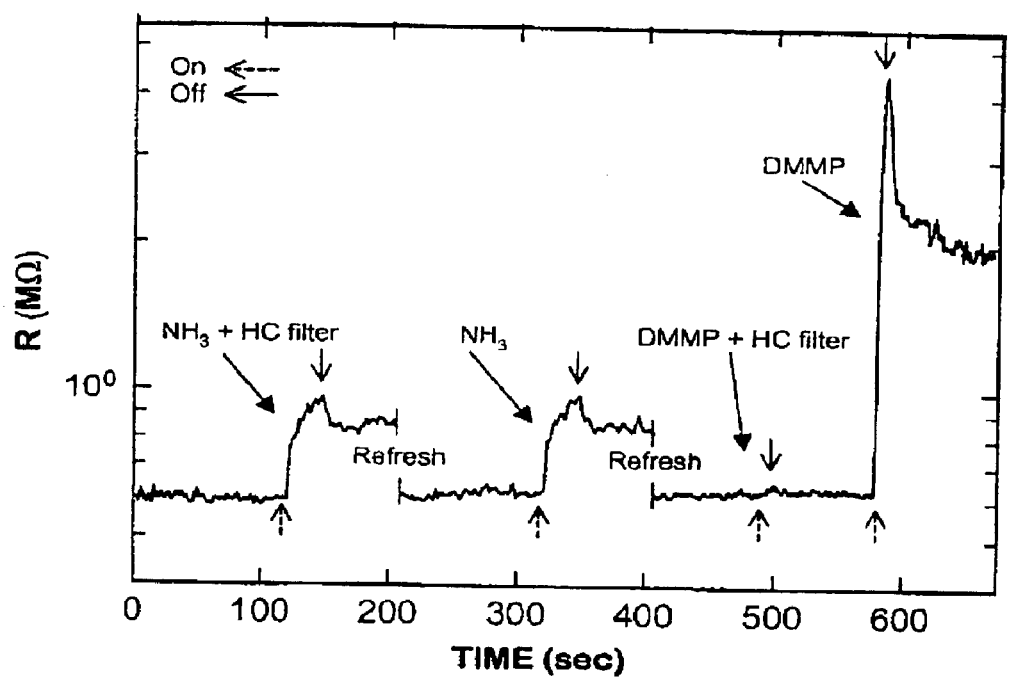
FIG. 12 shows the response of a sensor to $NH_3$ and DMMP that flows through a filter.

FIG. 12*a* shows the response of a sensor to $NH_3$ that was filtered with an HC-coated and an uncoated filter. The coated and uncoated responses are nearly identical indicating that the two filters equally affect the concentration of $NH_3$. When this same experiment was performed with DMMP vapor, there was a large difference in response (FIG. 12*b*) that indicates that the HC-coated filter is selectively removing the DMMP from the vapor stream. This simple example illustrates how chemoselective polymers can be combined with CNT-based sensors to provide additional chemical specificity.

Obviously, many modifications and variations of the present invention are possible in light of the above teachings. It is therefore to be understood that the claimed invention may be practiced otherwise than as specifically described.

We claim:

1. An electronic device comprising:
   a substrate;
   an interconnected network of carbon nanotubes on the surface of the substrate; and
   two or more electrical leads on the surface of the substrate;
   wherein the network forms an electrical connection between the leads; and
   wherein substantially none of the carbon nanotubes is in contact with both of the leads.

2. The device of claim 1, wherein the carbon nanotubes are single-walled carbon nanotubes.

3. The device of claim 1, wherein the network is a sub-monolayer of carbon nanotubes.

4. The device of claim 1, wherein the network is up to about 100 nm thick.

5. The device of claim 1, wherein the density of carbon nanotubes is at most about one thousand times the reciprocal of the square of the average length of the carbon nanotubes.

6. The device of claim 1,
   wherein the network comprises metallic single-walled carbon nanotubes; and
   wherein the density of the metallic single-walled carbon nanotubes is at most about the reciprocal of the square of the average length of the carbon nanotubes.

7. The device of claim 1, wherein the density of carbon nanotubes is at most about 10 $\mu m^{-2}$.

8. The device of claim 1, wherein the density of the carbon nanotubes is at least about one tenth the reciprocal of the square of the average length of the carbon nanotubes.

9. The device of claim 1, wherein the density of the carbon nanotubes is at least about 0.3 $\mu m^{-2}$.

10. The device of claim 1, wherein at least about 75% of the carbon nanotubes are at least partially in contact with the substrate.

11. The device of claim 1, wherein the network is semiconducting.

12. The device of claim 1, wherein the network further comprises a filler material.

13. The device of claim 12, wherein one or more electrical properties of the filler material are altered by the network.

14. The device of claim 12, wherein the filler material is a polymer.

15. The device of claim 1, wherein the distance between the leads is greater then the average length of the carbon nanotubes.

16. The device of claim 1, wherein the substrate is flexible.

17. The device of claim 1, further comprising a gate lead;
   wherein the device is a field effect transistor;
   wherein the leads electrically connected to the network form a source and a drain of the transistor; and
   wherein the network forms a conduction channel of the transistor.

18. The device of claim 17, further comprising an insulating material between the network and the gate.

19. The device of claim 17, wherein the gate is part of the substrate.

20. The device of claim 17, wherein the transistor has an on-to-off ratio of at least about $10^5$.

21. The device of claim 17, wherein the substrate is flexible.

22. The device of claim 17, wherein the conductivity of the network is modulated by a voltage applied to the gate.

23. The device of claim 1,
   wherein the network can be exposed to a gaseous sample; and
   wherein the resistivity of the network changes in response to the presence of one or more analytes in the sample.

24. The device of claim 23, wherein the substrate is flexible.

25. The device of claim 23, wherein substrate is a tube and the network is on the inside surface of the tube.

26. The device of claim 25, wherein the tube comprises quartz.

27. The device of claim 23, wherein the electrical leads comprise silver.

28. A display device comprising the device of claim 1.

29. The device of claim 1, wherein the substrate is substantially free of catalyst.

30. The device of claim 1, wherein at least one of the carbon nanotubes is in contact with neither of the leads.

31. The device of claim 1, wherein none of the nanotubes is in contact with both of the leads.

32. An electronic device comprising:
   a substrate;
   an interconnected network of nanofilaments on the surface of the substrate;
   two or more electrical leads on the surface of the substrate;
   wherein the network forms an electrical connection between the leads; and
   wherein substantially none of the nanofilaments is in contact with both of the leads.

33. The device of claim 32, wherein none of the nanofilaments is in contact with both of the leads.

34. The device of claim 32, wherein at least one of the nanofilaments is in contact with neither of the leads.

35. The device of claim 32, wherein the substrate is substantially free of catalyst.

36. An electronic device comprising:
   a substrate;
   an interconnected network of carbon nanotubes on the surface of the substrate; and
   two or more electrical leads;
   wherein the network forms an electrical connection between the leads;
   wherein the network can be exposed to a gaseous sample;
   wherein the resistivity of the network changes in response to the presence of one or more analytes in the sample; and
   wherein the substrate is a tube and the network is on the inside surface of the tube.

37. The device of claim 36, wherein the tube comprises quartz.

38. A field effect transistor comprising:
   a substrate;
   an interconnected network of carbon nanotubes on the surface of the substrate;
   a source lead;
   a drain lead, and
   a gate lead
   wherein the network forms a conduction channel of the transistor between the source and drain; and
   wherein the transistor has an on-to-off ratio of at least about $10^5$.

* * * * *